(12) United States Patent
Haley

(10) Patent No.: US 9,907,787 B2
(45) Date of Patent: *Mar. 6, 2018

(54) METHOD OF SUPPLEMENTING THE DIET AND AMELIORATING OXIDATIVE STRESS

(71) Applicant: EMERAMED LIMITED, Dublin (IE)

(72) Inventor: Boyd E. Haley, Nicholasville, KY (US)

(73) Assignee: EMERAMED LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/450,590

(22) Filed: Mar. 6, 2017

(65) Prior Publication Data
US 2017/0172990 A1   Jun. 22, 2017

Related U.S. Application Data

(60) Division of application No. 14/583,892, filed on Dec. 29, 2014, now Pat. No. 9,592,209, which is a continuation of application No. 12/630,259, filed on Dec. 3, 2009, now Pat. No. 8,950,583.

(60) Provisional application No. 61/201,060, filed on Dec. 6, 2008.

(51) Int. Cl.
| A61K 31/44 | (2006.01) |
| A61K 31/166 | (2006.01) |
| A61K 9/00 | (2006.01) |
| A61K 9/02 | (2006.01) |
| A61K 45/06 | (2006.01) |
| A23L 33/10 | (2016.01) |

(52) U.S. Cl.
CPC ........... *A61K 31/44* (2013.01); *A23L 33/10* (2016.08); *A61K 9/0014* (2013.01); *A61K 9/0019* (2013.01); *A61K 9/0043* (2013.01); *A61K 9/0053* (2013.01); *A61K 9/02* (2013.01); *A61K 31/166* (2013.01); *A61K 45/06* (2013.01); *A23V 2002/00* (2013.01)

(58) Field of Classification Search
None
See application file for complete search history.

(56) References Cited

U.S. PATENT DOCUMENTS

| 4,039,446 A | 8/1977 | Ban et al. |
| 4,281,086 A | 7/1981 | Gaul, Jr. et al. |
| 4,433,154 A | 2/1984 | Hirai |
| 4,508,838 A | 4/1985 | Buckl |
| 4,673,562 A | 6/1987 | Davison et al. |
| 4,751,286 A | 6/1988 | Packard et al. |
| 4,969,995 A | 11/1990 | Jackson et al. |
| 5,073,575 A | 12/1991 | Blanch et al. |
| 5,173,470 A | 12/1992 | Bruening et al. |
| 5,200,473 A | 4/1993 | Jeanneret-Gris |
| 5,494,935 A | 2/1996 | Miller et al. |
| 5,615,862 A | 4/1997 | Gaudette |
| 5,766,478 A | 6/1998 | Smith et al. |
| 6,013,246 A | 1/2000 | Langworth |
| 6,025,140 A | 2/2000 | Langel et al. |
| 6,586,600 B2 | 7/2003 | Atwood et al. |
| 6,852,369 B1 | 2/2005 | Atwood |
| 6,936,729 B2 | 8/2005 | Wolff et al. |
| 7,087,770 B2 | 8/2006 | Wolff et al. |
| 7,417,034 B2 | 8/2008 | Susilo |
| 7,482,160 B2 | 1/2009 | Monahan et al. |
| 2002/0136763 A1 | 9/2002 | Demopoulos et al. |
| 2004/0132101 A1 | 7/2004 | Lazar et al. |
| 2006/0099239 A1 | 5/2006 | Coleman et al. |
| 2006/0269488 A1 | 11/2006 | Ott |
| 2007/0026109 A1 | 2/2007 | Foulger |
| 2007/0077586 A1 | 4/2007 | Baggot |
| 2007/0191281 A1 | 8/2007 | Wolff et al. |
| 2011/0076246 A1 | 3/2011 | Haley et al. |
| 2011/0160150 A1 | 6/2011 | Haley et al. |
| 2011/0237525 A1 | 9/2011 | Haley et al. |

FOREIGN PATENT DOCUMENTS

| EP | 057797 | 8/1982 |
| WO | WO 2011038385 A2 | 3/2011 |

OTHER PUBLICATIONS

Aposhian "DMSA and DMPS—Water Soluble Antidotes for Heavy Metal Poisoning" Ann. Rev. Pharmacol Toxicol. 23: 193-213, 1983.
Guzzi et al. "Molecular mechanisms triggered by mercury" Toxicology 244: 1-12, 2008.
George et al. "Mercury Binding to the Chelation Therapy Agents DMSA and DMPS and the Rational Design of Custom Chelators for Mercury" Chem. Rev. Toxicol. 17: 909-1006, 2004.

(Continued)

*Primary Examiner* — Dennis Heyer
(74) *Attorney, Agent, or Firm* — King & Schickli, PLLC

(57) ABSTRACT

A method of supplementing a diet and ameliorating oxidative stress in a mammal includes administering a pharmaceutically effective amount of an active compound having the chemical structure:

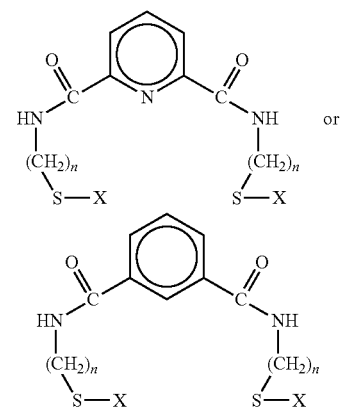

where n=1-4 and X is selected from the group consisting of hydrogen, lithium sodium, potassium, rubidium, cesium and francium.

12 Claims, No Drawings

(56) References Cited

OTHER PUBLICATIONS

Brandao et al. "DMPS and N-acetylcysteine induced renal toxicity in mice exposed to mercury" BioMetals 19:389-398, 2006.
Clarke et al. "Amelioration of acute mercury toxicity by a novel, non-toxic lipid soluble chelator N,N'bis-(2-mercaptoethyl)isophthalamide" Toxicological and Environmental Chemistry 2012: 1-25.
Flora et al. "Chelation in Metal Intoxication"; Int. J. Environ. Res. Public Health 2010, 7, 2745-2788, 2010.
Du Lin, et al.; "Glutathione and Oxidative Stress Tolerance of Plants" Shandong Science, Apr. 2008, vol. 21, No. 2, pp. 27-32; see Abstract.
Non-Final Office Action for U.S. Appl. No. 13/041,798 dated Dec. 31, 2012.
Anderson et al.; "Molecular Mechanisms of in Vivo Metal Chelation: Implications for Clinical Treatment of Metal Intoxications"; Environ. Health Perspect., vol. 110, Suppl. 5, pp. 887-890 (2002).
Final Office Action for U.S. Appl. No. 12/892,464 dated Nov. 28, 2012.
Non-Final Office Action for U.S. Appl. No. 13/565,047 dated Nov. 8, 2012.
William D. Roll; "Synthesis of Potential Antineoplastic Agents I"; Journal of Pharmaceutical Science, Jun. 1964, vol. 53, No. 6, pp 686-688.
Gelinsky, M. et al., Tripodal Pseudopeptides with Three Histidine or Cysteine Donors: Synthesis and Zinc Complexation, Inorg. Chem. 2002, 41, 2560-2564 (Apr. 5, 2002).
Ludlow, F.R. et al., Two-Vial, LC-MS; Identification of Ephedrine Receptors from a Solution-Phase Dynamic Combinatorial Library of over 9000 Components; J. Am. Chem. Soc. 2008, 130, 12218-12219 (Aug. 21, 2008).
West, K.R. et al., Dynamic Cominatorial Libraries of Disulfide Cages in Water, Organic Letters, 2005, 7(13), 2615-2618 (May 26, 2005); See Compound 5.
Wallen, E.A.A. et al., New Prolyl Oligopeptidase Inhibitors Developed from Dicarboxylic Acid Bis (L-prolyl-pyrrolidine) Amides, J. Med. Chem. 2003, 46, 4543-4551; (Sep. 4, 2003).

PCT/US2010/050512 International Search Report dated Jun. 21, 2011.
PCT/US2010/050512 Written Opinion dated Jun. 21, 2011.
Uwe Schröder, Lothar Beyer, and Joachim Sieler; "Synthesis and X-ray structure of a new silver(I) coordination polymer assembled as one-dimensional chains";Inorganic Chemistry Communications; vol. 3, Issue 11, Nov. 2000, pp. 630-633.
Matthew M. Matlock, Brock S. Howerton and David A. Atwood; "Irreversible precipitation of mercury and lead"; Journal of Hazardous Materials; vol. 84, Issue 1, Jun. 1, 2001, pp. 73-82.
Matthew M. Matlock, Brock S. Howerton, Kevin R. Henke and David A. Atwood; "A pyridine-thiol ligand with multiple bonding sites for heavy metal precipitation"; Journal of Hazardous Materials; vol. 82, Issue 1, Mar. 19, 2001, pp. 55-63.
Paul Römkens, Lucas Bouwman, Jan Japenga and Cathrina Draaisma; "Potentials and drawbacks of chelate-enhanced phytoremediation of soils"; Environmental Pollution; vol. 116, Issue 1, Jan. 2002, pp. 109-121.
International Preliminary Report on Patentability for International Application No. PCT/US2010/050512 dated Apr. 3, 2012.
Non-Final Office Action for U.S. Appl. No. 12/892,464 dated Feb. 2, 2012.
Kudo et al.; "Efficient Synthesis of Macrocycles by Oxidation of Cysteine-Based Dithiols"; Tetrahedron Letters (2001), vol. 42, Issue 44, pp. 7847-7850.
Non-Final Office Action for U.S. Appl. No. 12/731,415 dated May 24, 2012.
Non-Final Office Action for U.S. Appl. No. 12/630,259 dated Nov. 21, 2011.
Final Office Action for U.S. Appl. No. 12/630,259 dated Apr. 25, 2012.
Yamada et al.; "Solid-Phase Synthesis of Dehydroalanine Derivatives"; Tetrahedron Letters (1998), vol. 39, Issue 3-4, pp. 289-292.
Anderson; "Principles and Recent Developments in Chelation Treatment of Metal Intoxication" Chem. Rev. 1999, 99, 2683-2710.
Tandon, et al.; "Chelation in Metal Intoxication XXXVIII: Effect of Structurally Different Chellating Agents in Treatment of Nickel Intoxication in Rat" Fundamental and Applied Technology, 31, 141-148 *1996) Article No. 0085.
Gogolin, et al.; "Developmental Changes in the Biliary Excretion of Methylmercury and Glutathione"; Science, vol. 216, Apr. 2, 1982.

METHOD OF SUPPLEMENTING THE DIET AND AMELIORATING OXIDATIVE STRESS

This document is a divisional application of U.S. patent application Ser. No. 14/583,892, filed Dec. 29, 2014, which is a continuation of U.S. patent application Ser. No. 12/630,259 filed on Dec. 3, 2009, which claims the benefit of U.S. Provisional Patent Application Ser. No. 61/201,060 filed on Dec. 6, 2008, the full disclosures of which are incorporated herein by reference.

TECHNICAL FIELD

The present invention relates generally to the field of dietary supplements for mammals and, more particularly, to methods of supplementing a diet, removing heavy metals and other toxins and ameliorating oxidative stress.

BACKGROUND OF THE INVENTION

Heavy metals such as mercury, lead, cadmium and silver can bind to proteins on the proteins' incorporated cysteine residues which contain sulfhydryl or —SH groups. This abnormally inhibits or activates their biological properties. Further, a heavy metal binding specific proteins can induce damage that leads to overproduction or leakage of reactive oxygen species (ROSs) from their normal locations. These ROSs, mostly produced in the mitochondria of the cells of the body, then react with protein, nucleic acid (DNA, RNA) and lipid molecules in the healthy cell changing their property/chemistry and leading to unhealthy cells that may die or at least be unable to defend themselves from other stress factors such as viral infection. In addition to heavy metals there are many other chemical toxicants that can induce oxidative stress including, for example, radiation toxicity, acetominophin and dioxin. Further, it is well known that the oxidation of reduced glutathione (GSH) to oxidized glutathione (G-S-S-G) is one of the first biochemical signals for apoptotic cell death (or programmed cell death). The inadvertent oxidation of GSH by toxin produced ROSs could lead to increased GSSG and cell death also.

In order to medically prevent or reduce the problem, heavy metals must be excreted by natural means or complexed by medically based chelator compounds that render them biologically unavailable to elicit their toxic effects. To effect this removal and tightly bind the heavy metals, the treating compound must be able to effectively remove the metal from the single sulfur residue and bind it more tightly than is capable with only one sulfur to metal bond. That is, the compound must make more than one sulfur to metal bond to be able to prevent subsequent reaction or exchange of the complexed metal with other biomolecules. Additionally, the ideal chelating compound must have degrees of freedom of rotation of the sulfur bonds to be able to bind different heavy metals that have different coordination chemistries (e.g. different bond angles that confer tighter bonding). For example, $Hg^{2+}$ and $Pb^{2+}$ both can form two bonds with —SH groups, but the most stable binding of each metal would have different bond angles.

To be effective at treating both intracellular heavy metal toxicity and radiation toxicity as well as oxidative stress associated therewith, the treating compound has to be able to cross the cellular membrane with efficiency and, if the brain is involved, the treating compound must be able to cross the blood brain barrier. In order to be able to do this the compound has to be quite hydrophobic in nature in order to be able to pass through the lipid bilayer of the cell membrane to reach the site of heavy metal binding and intercept the ROS produced by the mitochondria before they react and damage cellular constituents. Further, the ideal treating compound must be of very low toxicity to cells and not disrupt membranes or biological pathways. In addition, the treating compound must be efficiently excreted from all tissues of the body in a non-toxic form. For example, if the treating compound binds mercury cation ($Hg^{2+}$) it must carry this metal ion out of the body and not distribute it to other organs such as the kidney.

The ideal treatment compound must also exhibit stability to air oxidation and breakdown so that the treating compound can be effectively stored and packaged for delivery to the patient in original, active form. The treating compound ideally must also be suited for ease of administration to a patient. Further, the treating compound must not deplete the body of essential metals such as zinc and copper. In addition, it should also have an adequately long plasma half-life such that it is possible to take eight hours rest and not have the treating compound significantly depleted from the plasma and tissues.

The present invention relates to methods of supplementing the diet of a mammal, removing heavy metals and other toxins from a mammal and ameliorating undesirable oxidative stress in a mammal.

SUMMARY OF THE INVENTION

In accordance with the purposes of the present invention as described herein, a method of supplementing a diet of a mammal is provided. That method comprises: administering to said mammal a pharmaceutically effective amount of a compound having a chemical formula:

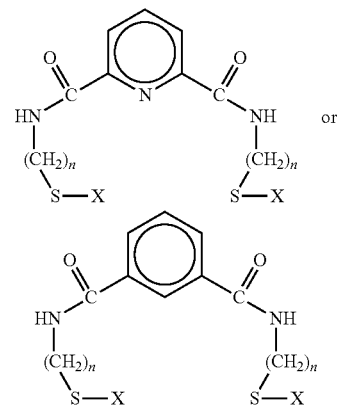

where n=1-4 and X is selected from the group consisting of hydrogen, lithium sodium, potassium, rubidium, cesium and francium.

In accordance with yet another aspect of the present invention, a method to remove heavy metals and toxins from a mammal comprises: administering to said mammal a pharmaceutically effective amount of a compound having a chemical formula:

where n=1-4 and X is selected from the group consisting of hydrogen, lithium sodium, potassium, rubidium, cesium and francium.

In accordance with yet another aspect of the present invention a method is provided for relieving oxidative stress in a mammal. That method comprises: administering to said mammal a pharmaceutically effective amount of a compound having a chemical formula:

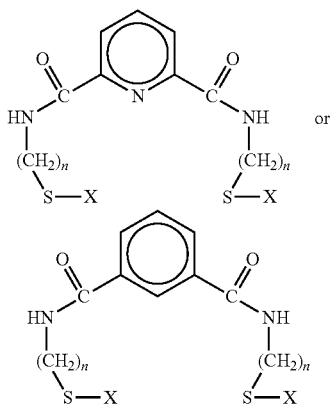

where n=1-4 and X is selected from the group consisting of hydrogen, lithium sodium, potassium, rubidium, cesium and francium.

In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention.

DETAILED DESCRIPTION OF THE
PREFERRED EMBODIMENTS OF THE
INVENTION

The present invention relates to various methods of supplementing the diet of a mammal, removing heavy metals and other toxins from a mammal and relieving or ameliorating oxidative stress in a mammal. Each of the methods relies upon administering to said mammal a pharmaceutically effective amount of a compound having a chemical formula:

where n=1-4 and X is selected from the group consisting of hydrogen, lithium sodium, potassium, rubidium, cesium and francium. The active compounds and their synthesis are described in detail in issued U.S. Pat. No. 6,586,600 to Atwood et al, the full disclosure of which is incorporated herein by reference.

While U.S. Pat. No. 6,586,600 discloses use of the compounds in question for removing heavy metals from the environment such as the natural water supply, it provides no teaching or suggestion that the compounds could be utilized in mammals as a dietary supplement, to ameliorate oxidative stress, to raise in vivo glutathione levels or to treat heavy metal or other toxicity. In fact, the compounds in U.S. Pat. No. 6,586,600 were mostly ineffective at treating environmental contaminations of heavy metal due to their insolubility in water and many organic solvents. The conventional wisdom is that any metal chelator has to be water soluble to be effective is evidenced by the currently known chelators such as dimercapopropane sulfonate (DMPS), dimercaptosuccinic acid (DMSA), ethylenediaminetetraacetic acid (EDTA) and even the natural mammalian heavy metal chelator glutathione. These observations made the use of the compounds questionable for any mammalian based treatment regarding the removal of charged toxic metals like $Hg^{2+}$, $Pb^{2+}$, and $Cd^{2+}$ which are water soluble and would most likely be located in the aqueous aspects of mammalian tissues. Additionally, any compound that is not water soluble nor soluble in most organic solvents would not be expected to pass the intestinal endothelial membrane barrier and enter the blood and tissues of the mammal. Further, the compound(s) would have to cross the cell membrane to be able to interact with and bind the intracellular located heavy metal responsible for the toxic effects. It would also have to be able to cross the blood brain barrier to be effective for any neurotoxic heavy metal effect. Then the excretion of the chelator-metal complex and the resulting toxicity of this complex would have to be effective and not cause any toxic effects. The disclosure in U.S. Pat. No. 6,586,600 suggests none of these desired performance parameters.

The pharmaceutically effective amount of the compounds in question may be administered in any appropriate manner including, but not limited to, oral administration, transdermal administration, nasal administration, intravenous administration and administration by suppository. The method of supplementing a diet of a mammal includes administering between about 0.5 and about 40.0 mg of the compound per kilogram of the mammal's total body weight per day although, due to the lack of toxicity higher dose levels are acceptable. The compound may be administered in combination with another antioxidant or chelator. That antioxidant may be selected from a group including but not limited to vitamin-E, vitamin-D, cysteine, cysteine, glutathione, lipoic acid and combinations thereof. In one particularly useful embodiment the compound has the chemical formula

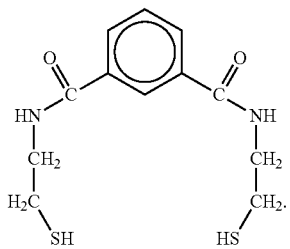

In the method of removing heavy metals and other toxins from a mammal, the compound is administered in an amount between about 0.5 and about 60.0 mg per kilogram of the mammal's total body weight per day. In this method the compound may be administered with a water soluble metal chelator. That water soluble metal chelator may be selected from a group consisting of glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof. It should be appreciated, however, that other water soluble metal chelators besides those listed could be utilized.

In the method of relieving oxidative stress in a mammal the compound may be administered orally, transdermally, nasally, intravenously, by suppository and other appropriate. Typically the compound is administered in an amount of between about 0.5 and about 100.0 mg of the compound per kilogram of the mammal's total body weight per day. The exceptionally low level of mammalian toxicity would also allow higher doses to be used in cases of acute toxicity or high oxidative stress. Here, it should also be noted that the present method may be used to treat oxidative stress resulting from virtually any cause or source including, but not limited to, heavy metal toxicity, drugs such as acetaminophen, xenobiotics, aging, infection, physical injury and disease.

These compounds are not used to directly produce intracellular glutathione and work primarily by salvaging naturally produced reduced glutathione (GSH) by the process of scavenging the intracellular ROSs preventing the oxidation to oxidized glutathione (GSSG). Also, the inhibitory binding of $Hg^{2+}$ and $Pb^{2+}$ and their removal from enzyme involved in the synthesis (e.g. glutamine synthetase) and recovery of GSH (e.g. glutathione reductase) would additionally aid in the recovery of GSH to optimal levels. In accordance with an additional aspect of the present invention the compound may be administered with a precursor of glutathione. That glutathione precursor may be selected from a group of precursors consisting of cysteine, glycine, glutamate and combinations thereof.

In yet another possible embodiment the compound is administered with a dietary supplement that supports glutathione synthesis. Such dietary supplements include, but are not limited to, whey protein, N-acetylcysteine, cysteine, glutathione, nicotine adenine dinucleotide ($NAD^+$), reduced nicotine adenine dinucleotide (NADH), glycylcysteine (gly-cyc), glutamylcysteine (glu-cys), and combinations thereof.

In one particularly useful embodiment the compound used for relieving oxidative stress has the chemical formula

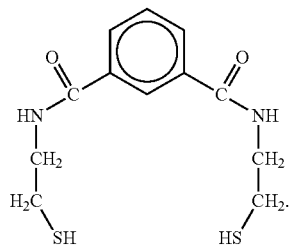

The compounds used in the present invention provide a number of unique benefits that make them attractive for use in methods of (a) supplementing the diet, (b) removing heavy metals and other toxins and (c) ameliorating oxidative stress in mammals. The compounds, and particularly, the compound

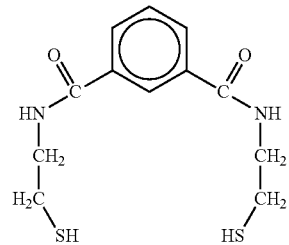

known as N,N'-bis(2-mercaptoethyl)isophthalamide or OSR, exhibit very low if any toxicity and do not adversely affect commonly used blood/urine tests commonly used to measure human health.

More specifically, OSR is without toxicity when administered in test animals at levels up to 5,000 mg per day. In fact, OSR is so non-toxic that an LD-50 could not be identified and was established as greater than 5 grams per kilogram body weight.

Advantageously OSR is lipid soluble and, accordingly, after entering the plasma can enter cells of all tissues, cross the blood brain barrier and enter the bone marrow. This is important because the damage caused by heavy metals and the oxidative stress produced by hydroxyl free radicals and other free radicals of the reactive oxygen species mostly occur in the intracellular space. In contrast, most dietary antioxidants are water soluble and cannot enter into cells effectively nor can they cross the blood/brain barrier.

As a further advantage, the lipid solubility of OSR increases the time it spends in the body allowing it to be more effective at chelating heavy metals and scavenging hydroxyl free radicals. The half-life of OSR in plasma of test animals was about six to seven hours whereas most water soluble antioxidants and chelators, such as resveratrol, DMPS, DMSA, and glutathione have a half-life of less than one to two hours as they are rapidly cleared by the kidneys or liver as they do not enter the cells and remain in the plasma.

It should also be appreciated that OSR is a pure compound that is not used as a substrate in any synthetic biochemical pathway of mammals. As such it does not disrupt any biochemical process. It simply partitions into the hydrophobic areas, binds heavy metals, reacts with free radicals eliminating them and is then excreted from the body primarily through the biliary transport system of the liver. It is also important to note that the two component parts of OSR consists of naturally, non-toxic, occurring benzoates and a catabolic product of cysteine metabolism that are combined to produce a product that has very low if any toxicity.

As should be appreciated from the following table, OSR has an exceptionally high ORAC (oxygen-radical-absorbance-capacity) score.

| Compound | Score (μmoleTE/100 g) |
|---|---|
| OSR#1 | 192,400 |
| Acai | 18,500 |
| Dark Chocolate | 13,120 |
| Pomegranates | 3,307 |
| Blueberries | 2,400 |
| Garlic | 1,939 |
| Cranberries | 1,750 |
| Spinach | 1,260 |
| Broccoli Florets | 890 |
| Kiwi Fruit | 610 |

The ORAC score is measured by a compound or elixer's ability to intercept reactive oxygen species, free radicals preventing them from oxidizing a water soluble fluorescent vitamin-E derivative. OSR has the ability in the body to protect vitamin-E (a fat soluble vitamin) and other fat soluble natural compounds such as lipids from damage by oxidizing free radicals since it partitions into the hydrophobic areas where they exist and reacts with free radicals more effectively than they do, thereby scavenging the hydroxyl free radicals and preventing them from doing damage. Significantly, vitamin-E has been recommended for Alzheimer's diseased subjects to prevent oxidizing damage to their brain membranes or membrane lipids due to vitamin-E's reactivity with hydroxyl free radicals. OSR is more capable of reacting with these radicals than vitamin-E and, accordingly, OSR should provide even better protection. In fact, OSR should salvage vitamin E and D in vivo.

Additionally, it is significant to note that when OSR is taken regularly, it does significantly increase the reduced (GSH) over oxidized (GSSG) glutathione ratio and increases total glutathione in the whole blood. Thus, more glutathione is available to scavenge free radicals and participate in the P-450 system to remove insoluble organic toxins from the membranes and cells. Thus, the body is better able to maintain a healthy glutathione level when the diet of the mammal is supplemented with OSR or other compounds of the present invention.

OSR has also been shown to bind injected mercury from mercury chloride and render this mercury non-toxic. Rats injected with 1-5 levels (or higher) of lethal doses of mercury chloride were protected from death by a single 10-fold excess above the mercury level of OSR dissolved in DMSO.

Rats given a 0.6 lethal dose of mercury chloride were protected from mercury induced toxic effects (blood in urine and feces, death, weight loss, ataxia) when given a 10-fold excess of OSR twenty-thirty minutes later. After five days, the mercury levels of many organs known to be mercury sensitive was measured. A toxic level of mercury still existed in the OSR treated rats but no toxic effects could be detected whereas the rats not given OSR showed these toxic effects. The OSR bound mercury was shown to be primarily excreted through the fecal route at a rate consistent with the P-450 system being involved.

OSR also has excellent stability when stored in sealed plastic test tubes with less than three percent breakdown occurring at sixteen months of storage at room temperature. Most antioxidants break down very rapidly when exposed to air or water but OSR is exceptional in this regards.

OSR also has only a very low odor level, much lower than most other sulfhydryl containing dietary compounds. Advantageously, this characteristic makes OSR more palatable for oral administration.

OSR also has an exceptionally high affinity for mercury, lead, arsenic and cadmium. Although OSR has good affinitive for the essential elements of copper, iron and zinc it seems as if the respective binding proteins of the body bind them tighter and treatment with OSR does not result in a significant lowering of these essential elements. Also, copper and zinc are primarily found in a water environment (hydrophilic aspects) of the body whereas OSR partitions into the hydrophobic aspects. This separation may play a role in the lack of OSR removing copper and zinc. However, in diseases with excess free copper, iron or zinc, OSR is likely to be able to bind and decrease the toxicity of these metals.

A kinetic study of OSR shows that it crosses the blood brain barrier, enters the intercellular space of all tissues tested which places OSR in the vicinity of the mitochondria and the cytoplasm. The mitochondria, especially if abnormal or damaged by heavy metals or radiation, are the main producers of the free radicals that cause cellular damage to the membranes, proteins or nucleic acids (DNA, RNA). Therefore, OSR is positioned to intercept these free radicals before they do damage and the ORAC scores show us OSR is exceptional at scavenging these toxic chemicals. Thus, OSR operates as an antioxidant in a more efficient and effective level than antioxidants generally known in the art.

It should also be appreciated that OSR is cleared from all tissues tested by over 90% twenty-four hours after ingestion. Therefore, no toxic build-up of OSR occurs in the mammal.

OSR also has a reactive site available for oxidation by the P-450 enzymes which allow OSR to be oxidized and modified as a sulfated, glycosylated or glutathione modified derivative by natural processes.

At the same time, OSR is better than glutathione delivered by IV or transdermally for increasing the intracellular level of glutathione. The rational behind this is based on the very low level of glutathione found in the plasma versus the intracellular levels which are 1,000 to 10,000 times higher. Any glutathione molecule that enters the blood by IV or transdermal delivery would be immediately bound and removed by the glutathione receptors in the liver that take glutathione labeled toxins out of the plasma and place them in the bile (biliary transport system). Glutathione in the blood would not remain long enough to enter cells where it could be used, plus it would have to enter in the face of a significant concentration gradient that would prevent this. This statement is based on the fact that many water insoluble toxicants are removed from the body by first oxidizing them, attaching glutathione (by the enzyme glutathione-s-transferase) to this oxidized site on the toxin, then actively transporting the glutathione labeled toxicant out of the cell and into the blood where it is removed by the glutathione receptors of the biliary transport system. In contrast, OSR enters all cells and due to its hydrophobic nature, inserts in some degree into the lipid membrane or other hydrophobic sites where it can scavenge hydroxyl free radicals, the major chemical species that oxidize glutathione and cause its levels to drop. OSR salvages naturally produced glutathione intracellularly enhancing its longevity and raising glutathione levels in vivo without having to battle transport across a membrane against a high gradient of glutathione.

Pharmaceutical compositions of the present invention may be prepared by combining a pharmaceutical effective amount of a compound having a chemical formula

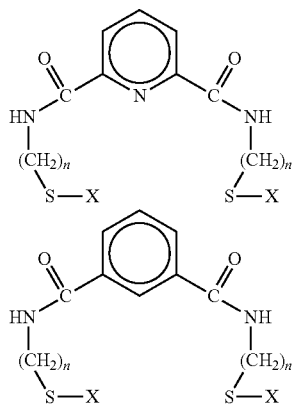

where n=1-4 and X is selected from the group consisting of hydrogen, lithium sodium, potassium, rubidium, cesium and francium, with an excipient. Substantially any suitable excipient may be utilized including but not limited to albumin, almond oil, ascorbic acid, benzoic acid, calcium stearate, canola oil, calcium carboxymethylcellulose, sodium carboxymethylcellulose, castor oil, hydrogenated castor oil, microcrystalline cellulose, corn oil, cotton seed oil, cyclodextrins, ethylene glycol palmitostearate, gelatin, glycerin, hydroxyethyl cellulose, hydroxyethylmethyl cellulose, hydroxypropyl cellulose, low-substituted hydroxypropyl cellulose, lanolin, linoleic acid, magnesium silicate, magnesium stearate, medium-chain triglycerides, mineral oil, olive oil, peanut oil, pectin, compressible sugar, sunflower oil, hydrogenated vegetable oil and water. In order to provide multiple antioxidant potential, the pharmaceutical compositions may further include other antioxidants including, but not limited to vitamin-E, vitamin-D, cysteine, glutathione, lipoic acid and combinations thereof. Further the pharmaceutical compositions may include a water soluble metal chelator to enhance removal of toxic metals both through the liver and kidney and with an enhanced rate. Substantially, any suitable water soluble metal chelator may be utilized including but not limited to glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof. Further, in order to further enhance the levels of glutathione in the subject, the pharmaceutical compositions may include a precursor of glutathione which may be selected from a group including but not limited to cysteine, glycine, glutamate and combinations thereof. Further pharmaceutical compositions may include a dietary supplement that supports glutathione synthesis. Substantially any appropriate dietary supplement that supports glutathione synthesis may be utilized including but not limited to whey protein, N-acetylcysteine, cysteine, glutathione, nicotine adenine dinucleotide (NAD$^+$), reduced nicotine adenine dinucleotide (NADH), glycylcysteine (gly-cys), glutamylcysteine (glu-cyc), and combinations thereof. Pharmaceutical compositions may also include various binders, preservatives, mineral supplements, bulking agents, diluents, carriers, flavoring agents that are widely known to be used in pharmaceutical compositions. Exemplary pharmaceutical compositions include between about 95.5 and about 85 weight percent active compound, between about 0.5 and about 15 weight percent excipient. The optional additional antioxidant(s) may be provided at between about 0 and about 50 weight percent. The optional additional water soluble metal chelator may be provided at between about 0 and about 20 weight percent. The optional additional precursor of glutathione may be provided at between about 0 and about 50 weight percent. Further the optionally additional dietary supplement that supports glutathione synthesis may be provided at between about 0 and about 50 weight percent. One or more of any of the optional additives may be included. The optional additive replaces a like percentage of the compound in the final composition.

Preferred dosage forms for oral administration include the isolated compounds in powder form. Such powders may be taken up with a swoop and spread onto food or mixed into drinks for easy consumption without bad taste. The pure compounds may be pre-mixed with certain dietary ingredients such as butter, olive oil, corn oil, albumin, whey or other foods which will help in absorption of the compounds by the mere process of dissolving them. Using OSR dissolved in corn oil, it was determined that it takes two hours post ingestion for the maximum level of OSR to show up in the plasma of all tested animals. Further, after 24 hours post-ingestion the OSR levels were shown to drop between 4-12% of the peak values seen at hour 2.

Some of the commercially available solubilizers that can be used for parenteral (injectable), oral, topical or intranasal delivery in different combinations and ratios according to need include: (a) co-solvents such as polyethylene glycol 300/400, Macrogol 300/400, Lutrol E300/E400, propylene glycol, Soluphor P and NMP; (b) PEG derivatives such as Cremophor RH40, Cremophor EL/ELP and Solutol HS-15; and (c) polyoxamers such as Lutrol F68, Lutrol F127, Lutrol Micro 68 and Lutrol Micro 127.

The pure compound may be encapsulated in several weight forms (e.g. 50, 100, 200, 500 mg/capsule) and taken orally. The pure compound may be mixed with excipients (e.g. microcrystalline cellulose, hypermellose, magnesium stearate) to provide a mixed material that can be efficiently encapsulated by machines for mass production at a rapid rate.

The pure compound may also be made into tablet form by mixing with common agents or binders used to induce adhesive properties for tablet formation.

OSR and any of the other hydrophobic compounds may be dissolved in simple oils and applied to the skin. The compounds dissolved in DMSO (dimethylsulfoxide) are rapidly taken up through the skin without local irritation.

OSR and the other compounds may be placed in suppository capsules either in powder form or dissolved in oils or as mixed with protein based material (e.g. human serum albumin) for delivery. OSR and the other compounds may also be dissolved in human serum albumin for intravenous delivery. Similarly, blood could be pulled from a patient and OSR or other compounds added to that blood before being returned to the patient.

The compositions and methods of the present invention may be accomplished by various means which are illustrated in the examples below. These examples are intended to be illustrative only as numerous modifications and variations will be apparent to those skilled in the art.

Example 1

In this example, 3.14 grams of 2-aminoethanethiol hydrochloride was dissolved in chloroform, and 3.88 ml of triethylamine were added. 2.81 grams of isophthaloyl chloride was then dissolved in chloroform under nitrogen. 2-aminoethanethiol hydrochloride and 1,3-isophthaloyl chloride, prepared as described supra, were then slowly mixed, and the resulting solution was stirred under nitrogen in an ice bath for several hours. The resulting solution was then filtered under nitrogen, and several water/chloroform extractions performed. Following removal of excess solvent by rotary evaporation or distillation, the resulting product was passed through a silica gel column using ethyl acetate/chloroform. Excess solvent was removed by rotary evaporation and vacuum-drying, resulting in a white precipitate. The resulting 1,3 benzene-thiol product had the formula:

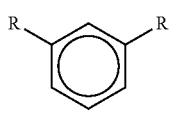

where R is an alkyl thio chain containing two methyl groups coupled through the carboxyl by an amide linkage.

Example 2

In this example, 2.76 grams of aminomethanethiol hydrochloride are dissolved in chloroform, and 7.72 ml of triethylamine are added. 2.81 grams of isophthaloyl chloride are then dissolved in chloroform under nitrogen. Aminomethanethiol hydrochloride and isophthaloyl chloride, prepared as described supra, are then slowly mixed, and the resulting solution is stirred under nitrogen in an ice bath for several hours. The resulting solution is then filtered under nitrogen, and several water/chloroform extractions are performed. Excess solvent is removed by rotary evaporation or distillation, and the resulting product is passed through a silica gel column using ethyl acetate/chloroform. Excess solvent is removed by rotary evaporation and vacuum-drying, resulting in a white precipitate. The resulting 1,3 benzene-thiol product has the formula:

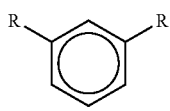

where R is an alkyl thiol chain containing one methyl group coupled through the carboxyl by an amide linkage.

Example 3

This example, 3.53 grams of 3-aminopropanethiol hydrochloride are dissolved in chloroform, and 7.72 ml of triethylamine are added. 2.81 grams of isophthaloyl chloride are then dissolved in chloroform under nitrogen. 3-aminopropanethiol hydrochloride and isophthaloyl chloride, prepared as described supra, are then slowly mixed, and the resulting solution is stirred under nitrogen in an ice bath for several hours. The resulting solution is then filtered under nitrogen, and several water/chloroform extractions are performed. Excess solvent is removed by rotary evaporation or distillation, and the resulting product is passed through a silica gel column using ethyl acetate/chloroform. Excess solvent is removed by rotary evaporation and vacuum-drying, resulting in a white precipitate. The resulting 1,3 benzene-thiol product has the formula:

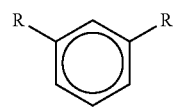

where R is an alkyl thiol chain containing three methyl groups coupled through the carboxyl by an amide linkage.

Example 4

In this example, 3.92 grams of 4-aminobutanethiol hydrochloride are dissolved in chloroform, and 7.72 ml of triethylamine are added. 2.81 grams of isophthaloyl chloride are then dissolved in chloroform under nitrogen. 4-aminobutanethiol hydrochloride and isophthaloyl chloride, prepared as described supra, are then slowly mixed, and the resulting solution is stirred under nitrogen in an ice bath for several hours. The resulting solution is then filtered under nitrogen, and several water/chloroform extractions are performed. Excess solvent is removed by rotary evaporation or distillation, and the resulting product is passed through a silica gel column using ethyl acetate/chloroform. Excess solvent is removed by rotary evaporation and vacuum-drying, resulting in a white precipitate. The resulting 1,3 benzene-thiol product has the formula:

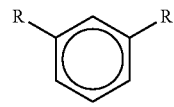

where R is an alkyl thiol chain containing four methyl groups coupled through the carboxyl by an amide linkage.

Example 5

In this example, 5 grams of 2,6 pyridine dicarbonyl dichloride were dissolved in chloroform under nitrogen. 5.56 grams of 2-aminothioethane thiol hydrochloride were also dissolved in chloroform under nitrogen, and slowly added to the acid chloride solution in an ice bath. Approximately 13.66 ml of triethylamine were added. The resulting mixture was stirred under nitrogen for 2-4 hours. The resulting yellow/brown solution was filtered under nitrogen, extracted three times with water/chloroform, refiltered under nitrogen, and excess solvent was removed by rotary evaporation or distillation. The resulting product was redissolved in chloroform and passed through a silica gel column using 70% ethyl acetate/30% chloroform. The resulting white precipitate was a 2,6 pyridine thiol product with the formula:

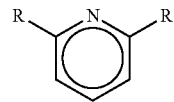

where R is an alkyl thiol chain containing two methyl groups coupled through the carboxyl by an amide linkage.

Example 6

Effect of daily administration of OSR on key biochemical parameters. Table 6-1 shows that the redox ratio (GSH/GSSG) was dramatically improved in 10 subjects taking 200 mg of OSR per day for a period of approximately 60 days. Improvement was seen in the first 30 days and continued into the second month. Also, the major improvement seemed to result from the very significant decrease in oxidized glutathione (GSSG) instead of a total increase in all forms of glutathione. This would be best explained by OSR scavenging hydroxyl free radicals salvaging the GSH by preventing its oxidation to GSSG. This change occurred in 10 of 10 subjects.

TABLE 6-1

Effect of OSR on blood GSH, GSSG levels and GSH/GSSG ratios.

| | tGSH/GSSG | | | GSSG | | | GSH | | |
|---|---|---|---|---|---|---|---|---|---|
| | Time (months) | | | | | | | | |
| Patient # | 0 | 1 | 2 | 0 | 1 | 2 | 0 | 1 | 2 |
| 1 | 40.3 | 53.6 | 87.1 | 0.133 | 0.129 | 0.065 | 5.4 | 6.9 | 5.7 |
| 2 | 42.9 | 37.5 | 87.7 | 0.159 | 0.209 | 0.117 | 6.8 | 7.8 | 10.3 |
| 3 | 24.8 | 32.3 | 64.5 | 0.167 | 0.154 | 0.083 | 4.1 | 5.0 | 5.4 |
| 4 | 14.8 | 22.1 | 28.6 | 0.482 | 0.282 | 0.189 | 7.1 | 6.2 | 5.4 |
| 5 | 66.9 | 73.7 | 93.7 | 0.108 | 0.103 | 0.067 | 7.2 | 7.6 | 6.3 |
| 6 | 14.1 | 33.4 | 38.5 | 0.308 | 0.154 | 0.137 | 4.3 | 5.2 | 5.3 |
| 7 | 36.9 | 40.3 | 44.9 | 0.127 | 0.113 | 0.081 | 4.7 | 4.6 | 3.6 |
| 8 | 17.3 | 36.2 | 28.7 | 0.236 | 0.146 | 0.195 | 4.1 | 5.3 | 5.6 |
| 9 | 11.4 | 16.9 | 48.9 | 0.521 | 0.396 | 0.139 | 5.9 | 6.7 | 6.8 |
| 10 | 15.8 | 42.8 | 69.6 | 0.283 | 0.165 | 0.119 | 4.5 | 7.1 | 8.3 |
| Average | 28.5 | 38.9 | 59.2 | 0.252 | 0.185 | 0.119 | 5.4 | 6.2 | 6.3 |

This data was collected from a single clinic where the subjects varied in age from 8 to 73 years old and were 5 male and 5 female. All were in reasonable health with no obvious bacterial infections. GSH/GSSG ratios increased in all primarily due to the drop in GSSG levels in all subjects. GSH levels remained relatively constant and increased slightly in 7 of 10. The average tGSH/GSSG ratio almost doubled caused by a near average halving of the GSSG levels.

To determine if OSR changed the level of cysteine, the rate limiting amino acid in glutathione synthesis, the level of all thiol containing amino acids was done for the same 10 patients for a two month period. As seen in Table 6-2, there was no significant change in the amino acid levels for any of the patients with one exception. The homocysteine level was high in patient #9, a 72 year old male diagnosed with Alzheimer's disease, over the two month testing his levels dropped to near normal levels. These results imply that OSR increases GSH levels by scavenging hydroxyl free radicals and salvaging GSH, not by supplying more cysteine for GSH synthesis.

No significant consistent changes in cysteine, methionine or homocysteine levels were observed. The possible exception was the homocysteine levels in patient #9, a male with Alzheimer's disease.

As seen in Table 6-3, glutathione-S-transferase (GST) was consistently elevated in all 10 patients in this study after OSR treatment. GST is an enzyme that uses glutathione (GSH) as a substrate to covalently modify certain organic toxins by 'transferring GSH' to a P-450 enzyme oxidized site on the toxin. This results in a GSH-toxin complex that is now water soluble and capable of being excreted from the body. GST was non-detectable in all 10 patients at the start of the study and was detectable in all 10 patients at the end of the study. The change in the redox level most likely had something to do with the appearance of this enzyme. It is a common mechanism in cellular regulation that the lowering of a substrate (e.g. glutathione) needed at several locations results in the suppressed expression of the enzyme (e.g. GST) that use this substrate for reactions that are less necessary to support survival. The buildup of GSH most likely induces the expression of GST and this buildup accounts for the induction of new GST synthesis.

TABLE 6-3

Effect of OSR on Glutathione-S-transferase (GST) levels (ng/ml)
GST

| | Time (months) | | |
|---|---|---|---|
| Patient # | 0 | 1 | 2 |
| 1 | L | L | 0.48 |
| 2 | L | L | 0.48 |
| 3 | L | 0.46 | 0.43 |
| 4 | L | L | 0.53 |
| 5 | L | L | 0.43 |
| 6 | L | L | 0.37 |
| 7 | L | L | 0.32 |
| 8 | L | 0.58 | 0.43 |
| 9 | L | L | 0.63 |
| 10 | L | L | 0.43 |

GST activities increased in every patient. Detection levels were 0.4 for normals to 3.1 for a high level for GST.

Example 7

Protective effects of OSR on rats injected subcutaneously with mercuric chloride.

TABLE 6-2

Effect of OSR on blood sulfur containing amino acid levels (cysteine, methionine, homocysteine).

| | Cysteine | | | Methionine | | | Homocysteine | | | |
|---|---|---|---|---|---|---|---|---|---|---|
| | AGE Time (months) | | | | | | | | | |
| Patient # | 0 | 1 | 2 | 0 | 1 | 2 | 0 | 1 | 2 | |
| 1 | 200 | 212 | 202 | 14.8 | 15.4 | 16.4 | 4.63 | 5.51 | 5.31 | 8 wm |
| 2 | 170 | 167 | 169 | 20.7 | 22.7 | 26.0 | 5.74 | 5.13 | 5.04 | 9 wf |
| 3 | 240 | 231 | 260 | 22.1 | 22.6 | 26.3 | 5.16 | 5.91 | 6.32 | 9 wf |
| 4 | 237 | 250 | 185 | 22.1 | 19.4 | 30.9 | 7.92 | 8.36 | 9.18 | 11 wm |
| 5 | 231 | 225 | 244 | 20.9 | 24.0 | 30.4 | 6.07 | 5.31 | 5.75 | 12 wm |
| 6 | 269 | 217 | 248 | 16.02 | 16.4 | 32.0 | 9.95 | 8.61 | 6.18 | 32 wf |
| 7 | 282 | 246 | 251 | 23.5 | 26.6 | 27.2 | 7.26 | 7.45 | 8.78 | 45 wm |
| 8 | 304 | 243 | 290 | 15.4 | 17.2 | 25.4 | 9.69 | 9.27 | 9.11 | 71 wf |
| 9 | 344 | 255 | 317 | 20.5 | 28.3 | 31.2 | 21.2 | 13.9 | 12.8* | 72 male AD |
| 10 | 288 | 253 | 324 | 21.1 | 23.1 | 33.7 | 11.4 | 12.6 | 16.1 | 73 wf |

OSR

The mercury chloride LD 50 for rats is reported to be 3.2 mg/kg body weight intraperitoneal. Our experiments were designed around this value.

For each of the experiments nine, 5-7 weeks old, rats were chosen. They were divided into three groups and they were fed rat chow and water ad libitum.

The mercuric chloride was dissolved in PBS/DMSO and injected intraperitoneally at time zero.

The compound OSR was dissolved in 0.75 ml DMSO and 0.25 ml PBS. Injection was subcutaneous under the skin covering the stomach. These were done 20 min. after the injection of the mercuric chloride.

TABLE 7-1

Dosage of Mercury chloride at 2 mg/kg body weight.

| | OSR GROUP | | | CONTROL GROUP | | |
|---|---|---|---|---|---|---|
| | Rat 1 | Rat 2 | Rat 3 | Rat 1 | Rat 2 | Rat 3 |
| Weight (gram) | 230 | 242 | 238 | 237 | 242 | 246 |
| Mercury chloride (mg)* | 0.46 | 0.48 | 0.48 | 0.47 | 0.48 | 0.49 |
| OSR (mg)** | 32.66 | 34.4 | 33.8 | 0 | 0 | 0 |
| 0 hr | A | A | A | A | A | A |
| 6 hr | A | A | A | A | A | A |
| 12 hr | A | A | A | A | A | D |
| 24 hr | A | A | A | D | D | — |
| 48 hr | A | A | A | — | — | — |
| 1 week | A | A | A | — | — | — |

*= Equivalent to 2 mg/kg body weight.
**= Equivalent to 0.5 millimoles/kg body weight
D = Dead; A = Alive

TABLE 7-2

Dosage of mercury 14 mg/kg

| | OSR GROUP | | | CONTROL GROUP | | |
|---|---|---|---|---|---|---|
| | Rat 1 | Rat 2 | rat 3 | Rat 1 | Rat 2 | Rat 3 |
| Weight (in gram) | 229.0 | 243.0 | 242.0 | 243.0 | 238.0 | 246.0 |
| Mercury chloride*[1] | 3.2 | 3.4 | 3.4 | 3.4 | 3.3 | 3.4 |
| OSR (mg)*[2] | 65.0 | 69.0 | 68.7 | 0.0 | 0.0 | 0.0 |
| 0 hr | A | A | A | A | A | A |
| 6 hr | A | A | A | D | D | A |
| 12 hr | A | A | A | — | — | D |
| 24 hr | A | A | A | — | — | — |
| 48 hr | D | A | A | — | — | — |
| 1 week | — | A | A | — | — | — |

*[1]= Equivalent to 14 mg/kg body weight.
*[2]= Equivalent to 1 mM/kg body weight
D = Dead; A = Alive Example 8

Mixture with oil. OSR may be admixed with emu oil or another oil not typically used as a pharmaceutical-grade excipient but known in the art to be useful in the cosmetic and or non-allopathic medical arts, thereby making an OSR-oil mixture useful as an antioxidant and/or detoxicant.

Example 9

Functional food. OSR may be admixed with a food known in the art, thereby making an OSR-food mixture useful as an antioxidant or detoxicant functional food.

Example 10

Medicament useful for treating disease. A therapeutically effective medicament composition containing OSR may be administered orally to a human subject in whom it is desired to ameliorate the effect of any disease known to be associated with oxidative stress, including without limitation each disease listed in Chapter 9 of Halliwell and Gutteridge 2007, op. cit. (Aspects of the relationship between oxidative stress and aging are discussed in Chapter 10 of that work.)

Example 11

Medicament and/or preparation of dosage form. To prepare a medicament and/or suitable dosage form, OSR may be admixed and/or contacted with one or more of the excipients listed in Table 11-1.

TABLE 11-1

| Excipients |
|---|
| Acacia |
| Acesulfame Potassium |
| Acetic Acid, Glacial |
| Acetone |
| Acetyltributyl Citrate |
| Acetyltriethyl Citrate |
| Agar |
| Albumin |
| Alcohol |
| Alginic Acid |
| Aliphatic Polyesters |
| Alitame |
| Almond Oil |
| Alpha Tocopherol |
| Aluminum Hydroxide Adjuvant |
| Aluminum Oxide |
| Aluminum Phosphate Adjuvant |
| Aluminum Stearate |
| Ammonia Solution |
| Ammonium Alginate |
| Ascorbic Acid |
| Ascorbyl Palmitate |
| Aspartame |
| Attapulgite |
| Bentonite |
| Benzalkonium Chloride |
| Benzethonium Chloride |
| Benzoic Acid |
| Benzyl Alcohol |
| Benzyl Benzoate |
| Boric Acid |
| Bronopol |
| Butylated Hydroxyanisole |
| Butylated Hydroxytoluene |
| Butylparaben |
| Calcium Alginate |
| Calcium Carbonate |
| Calcium Phosphate, Dibasic Anhydrous |

TABLE 11-1-continued

| Excipients |
|---|
| Calcium Phosphate, Dibasic Dihydrate |
| Calcium Phosphate, Tribasic |
| Calcium Stearate |
| Calcium Sulfate |
| Canola Oil |
| Carbomer |
| Carbon Dioxide |
| Carboxymethylcellulose Calcium |
| Carboxymethylcellulose Sodium |
| Carrageenan |
| Castor Oil |
| Castor Oil, Hydrogenated |
| Cellulose, Microcrystalline |
| Cellulose, Powdered |
| Cellulose, Silicified Microcrystalline |
| Cellulose Acetate |
| Cellulose Acetate Phthalate |
| Ceratonia |
| Cetostearyl Alcohol |
| Cetrimide |
| Cetyl Alcohol |
| Cetyrpyridinium Chloride |
| Chitosan |
| Chlorhexidine |
| Chlorobutanol |
| Chlorocresol |
| Chlorodifluoroethane (HCFC) |
| Chlorofluorocarbons (CFC) |
| Chloroxylenol |
| Cholesterol |
| Citric Acid Monohydrate |
| Colloidal Silicon Dioxide |
| Coloring Agents |
| Copovidone |
| Corn Oil |
| Cottonseed Oil |
| Cresol |
| Croscarmellose Sodium |
| Crospovidone |
| Cyclodextrins |
| Cyclomethicone |
| Denatonium Benzoate |
| Dextrates |
| Dextrin |
| Dextrose |
| Dibutyl Phthalate |
| Dibutyl Sebacate |
| Diethanolamine |
| Diethyl Phthalate |
| Difluoroethane (HFC) |
| Dimethicone |
| Dimethyl Ether |
| Dimethyl Phthalate |
| Dimethyl Sulfoxide |
| Dimethylacetamide |
| Disodium Edetate |
| Docusate Sodium |
| Edetic Acid |
| Erythorbic Acid |
| Erythritol |
| Ethyl Acetate |
| Ethyl Lactate |
| Ethyl Maltol |
| Ethyl Oleate |
| Ethyl Vanillin |
| Ethylcellulose |
| Ethylene Glycol Palmitostearate |
| Ethylene Vinyl Acetate |
| Ethylparaben |
| Fructose |
| Fumaric Acid |
| Gelatin |
| Glucose, Liquid |
| Glycerin |
| Glyceryl Behenate |
| Glyceryl Monooleate |
| Glyceryl Monostearate |
| Glyceryl Palmitostearate |
| Glycofurol |
| Guar Gum |
| Hectorite |
| Heptafluoropropane (HFC) |
| Hexetidine |
| Hydrocarbons (HC) |
| Hydrochloric Acid |
| Hydroxyethyl Cellulose |
| Hydroxyethylmethyl Cellulose |
| Hydroxypropyl Cellulose |
| Hydroxypropyl Cellulose, Low-substituted |
| Hydroxypropyl Starch |
| Hypromellose |
| Hypromellose Acetate Succinate |
| Hypromellose Phthalate |
| Imidurea |
| Inulin |
| Iron Oxides |
| Isomalt |
| Isopropyl Alcohol |
| Isopropyl Myristate |
| Isopropyl Palmitate |
| Kaolin |
| Lactic Acid |
| Lactitol |
| Lactose, Anhydrous |
| Lactose, Monohydrate |
| Lactose, Spray-Dried |
| Lanolin |
| Lanolin, Hydrous |
| Lanolin Alcohols |
| Laurie Acid |
| Lecithin |
| Leucine |
| Linoleic Acid |
| Macrogol 15 Hydroxystearate |
| Magnesium Aluminum Silicate |
| Magnesium Carbonate |
| Magnesium Oxide |
| Magnesium Silicate |
| Magnesium Stearate |
| Magnesium Trisilicate |
| Malic Acid |
| Maltitol |
| Maltitol Solution |
| Maltodextrin |
| Maltol |
| Maltose |
| Mannitol |
| Medium-chain Triglycerides |
| Meglumine |
| Menthol |
| Methylcellulose |
| Methylparaben |
| Mineral Oil |
| Mineral Oil, Light |
| Mineral Oil and Lanolin Alcohols |
| Monoethanolamine |
| Monosodium Glutamate |
| Monothioglycerol |
| Myristic Acid |
| Neohesperidin Dihydrochalcone |
| Nitrogen |
| Nitrous Oxide |
| Octyldodecanol |
| Oleic Acid |
| Oleyl Alcohol |
| Olive Oil |
| Palmitic Acid |
| Paraffin |
| Peanut Oil |
| Pectin |
| Petrolatum and Lanolin Alcohols |
| Petrolatum |
| Phenol |
| Phenoxyethanol |
| Phenylethyl Alcohol |
| Phenylmercuric Acetate |

TABLE 11-1-continued

| Excipients |
|---|
| Phenylmercuric Borate |
| Phenylmercuric Nitrate |
| Phosphoric Acid |
| Polacrilin Potassium |
| Poloxamer |
| Polycarbophil |
| Polydextrose |
| Polyethylene Glycol |
| Polyethylene Oxide |
| Polymethacrylates |
| Poly(methyl vinyl ether/maleic anhydride) |
| Polyoxyethylene Alkyl Ethers |
| Polyoxyethylene Castor Oil Derivatives |
| Polyoxyethylene Sorbitan Fatty Acid Esters |
| Polyoxyethylene Stearates |
| Polyvinyl Acetate Phthalate |
| Polyvinyl Alcohol |
| Potassium Alginate |
| Potassium Benzoate |
| Potassium Bicarbonate |
| Potassium Chloride |
| Potassium Citrate |
| Potassium Hydroxide |
| Potassium Metabisulfite |
| Potassium Sorbate |
| Povidone |
| Propionic Acid |
| Propyl Gallate |
| Propylene Carbonate |
| Propylene Glycol |
| Propylene Glycol Alginate |
| Propylparaben |
| 2-Pyrrolidone |
| Raffinose |
| Saccharin |
| Saccharin Sodium |
| Saponite |
| Sesame Oil |
| Shellac |
| Simethicone |
| Sodium Acetate |
| Sodium Alginate |
| Sodium Ascorbate |
| Sodium Benzoate |
| Sodium Bicarbonate |
| Sodium Borate |
| Sodium Chloride |
| Sodium Citrate Dihydrate |
| Sodium Cyclamate |
| Sodium Hyaluronate |
| Sodium Hydroxide |
| Sodium Lactate |
| Sodium Lauryl Sulfate |
| Sodium Metabisulfite |
| Sodium Phosphate, Dibasic |
| Sodium Phosphate, Monobasic |
| Sodium Propionate |
| Sodium Starch Glycolate |
| Sodium Stearyl Fumarate |
| Sodium Sulfite |
| Sorbic Acid |
| Sorbitan Esters (Sorbitan Fatty Acid Esters) |
| Sorbitol |
| Soybean Oil |
| Starch |
| Starch, Pregelatinized |
| Starch, Sterilizable Maize |
| Stearic Acid |
| Stearyl Alcohol |
| Sucralose |
| Sucrose |
| Sugar, Compressible |
| Sugar, Confectioner's |
| Sugar Spheres |
| Sulfobutylether β-Cyclodextrin |
| Sulfuric Acid |
| Sunflower Oil |
| Suppository Bases, Hard Fat |
| Talc |
| Tartaric Acid |
| Tetrafluoroethane (HFC) |
| Thaumatin |
| Thymol |
| Titanium Dioxide |
| Tragacanth |
| Trehalose |
| Triacetin |
| Tributyl Citrate |
| Triethanolamine |
| Triethyl Citrate |
| Vanillin |
| Vegetable Oil, Hydrogenated |
| Water |
| Wax, Anionic Emulsifying |
| Wax, Carnauba |
| Wax, Cetyl Esters |
| Wax, Microcrystalline |
| Wax, Nonionic Emulsifying |
| Wax, White |
| Wax, Yellow |
| Xanthan Gum |
| Xylitol |
| Zein |
| Zinc Acetate |
| Zinc Stearate |

Example 12

Dosage form. A suitable dosage form for administration of OSR or other active compound may be chosen from among the dosage forms listed in Table 12-1.

TABLE 12-1

| NAME | DEFINITION |
|---|---|
| Dosage forms | |
| AEROSOL | A product that is packaged under pressure and contains therapeutically active ingredients that are released upon activation of an appropriate valve system; it is intended for topical application to the skin as well as local application into the nose (nasal aerosols), mouth (lingual aerosols), or lungs (inhalation aerosols). |
| AEROSOL, POWDER | A product that is packaged under pressure and contains therapeutically active ingredients, in the form of a powder, that are released upon activation of an appropriate valve system. |
| BAR, CHEWABLE | A solid dosage form usually in the form of a rectangle that is meant to be chewed. |
| CAPSULE | A solid oral dosage form consisting of a shell and a filling. The shell is composed of a single sealed enclosure, or two halves that fit together and which are sometimes sealed with a band. Capsule shells may be made from gelatin, starch, or cellulose, or other suitable materials, may be soft or hard, and are filled with solid or liquid ingredients that can be poured or squeezed. |
| CAPSULE, COATED | A solid dosage form in which the drug is enclosed within either a hard or soft soluble container or "shell" made from a suitable form of gelatin; additionally, the capsule is covered in a designated coating. |
| CAPSULE, COATED PELLETS | A solid dosage form in which the drug is enclosed within either a hard or soft soluble container or "shell" made from a suitable form of gelatin; the drug itself is in the form of granules to which varying amounts of coating have been applied. |

TABLE 12-1-continued

Dosage forms

| NAME | DEFINITION |
|---|---|
| CAPSULE, COATED, EXTENDED RELEASE | A solid dosage form in which the drug is enclosed within either a hard or soft soluble container or "shell" made from a suitable form of gelatin; additionally, the capsule is covered in a designated coating, and which releases a drug (or drugs) in such a manner to allow at least a reduction in dosing frequency as compared to that drug (or drugs) presented as a conventional dosage form. |
| CAPSULE, DELAYED RELEASE | A solid dosage form in which the drug is enclosed within either a hard or soft soluble container made from a suitable form of gelatin, and which releases a drug (or drugs) at a time other than promptly after administration. Enteric-coated articles are delayed release dosage forms. |
| CAPSULE, DELAYED RELEASE PELLETS | A solid dosage form in which the drug is enclosed within either a hard or soft soluble container or "shell" made from a suitable form of gelatin; the drug itself is in the form of granules to which enteric coating has been applied, thus delaying release of the drug until its passage into the intestines. |
| CAPSULE, EXTENDED RELEASE | A solid dosage form in which the drug is enclosed within either a hard or soft soluble container made from a suitable form of gelatin, and which releases a drug (or drugs) in such a manner to allow a reduction in dosing frequency as compared to that drug (or drugs) presented as a conventional dosage form. |
| CAPSULE, FILM COATED, EXTENDED RELEASE | A solid dosage form in which the drug is enclosed within either a hard or soft soluble container or "shell" made from a suitable form of gelatin; additionally, the capsule is covered in a designated film coating, and which releases a drug (or drugs) in such a manner to allow at least a reduction in dosing frequency as compared to that drug (or drugs) presented as a conventional dosage form. |
| CAPSULE, GELATIN COATED | A solid dosage form in which the drug is enclosed within either a hard or soft soluble container made from a suitable form of gelatin; through a banding process, the capsule is coated with additional layers of gelatin so as to form a complete seal. |
| CAPSULE, LIQUID FILLED | A solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle. |
| CONCENTRATE | A liquid preparation of increased strength and reduced volume which is usually diluted prior to administration. |
| CORE, EXTENDED RELEASE | An ocular system placed in the eye from which the drug diffuses through a membrane at a constant rate over a specified period. |
| CREAM | An emulsion, semisolid[3] dosage form, usually containing >20% water and volatiles5 and/or <50% hydrocarbons, waxes, or polyols as the vehicle. This dosage form is generally for external application to the skin or mucous membranes. |
| CREAM, AUGMENTED | A cream dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| DRUG DELIVERY SYSTEM | Modern technology, distributed with or as a part of a drug product that allows for the uniform release or targeting of drugs to the body. |
| ELIXIR | A clear, pleasantly flavored, sweetened hydro alcoholic liquid containing dissolved medicinal agents; it is intended for oral use. |
| EMULSION | A dosage form consisting of a two-phase system comprised of at least two immiscible liquids[1], one of which is dispersed as droplets (internal or dispersed phase) within the other liquid (external or continuous phase), generally stabilized with one or more emulsifying agents. (Note: Emulsion is used as a dosage form term unless a more specific term is applicable, e.g. cream, lotion, ointment.) |
| ENEMA | A rectal preparation for therapeutic, diagnostic, or nutritive purposes. |
| EXTRACT | A concentrated preparation of vegetable or animal drugs obtained by removal of the active constituents of the respective drugs with a suitable menstrua, evaporation of all or nearly all of the solvent, and adjustment of the residual masses or powders to the prescribed standards. |
| FIBER, EXTENDED RELEASE | A slender and elongated solid thread-like substance that delivers drug in such a manner to allow a reduction in dosing frequency as compared to that drug (or drugs) presented as a conventional dosage form. |
| FILM, SOLUBLE | A thin layer or coating which is susceptible to being dissolved when in contact with a liquid. |
| FOR SOLUTION | A product, usually a solid, intended for solution prior to administration. |
| FOR SUSPENSION | A product, usually a solid, intended for suspension prior to administration. |
| FOR SUSPENSION, EXTENDED RELEASE | A product, usually a solid, intended for suspension prior to administration; once the suspension is administered, the drug will be released at a constant rate over a specified period. |
| GEL | A semisolid[3] dosage form that contains a gelling agent to provide stiffness to a solution or a colloidal dispersion.[4] A gel may contain suspended particles. |
| GLOBULE | Also called pellets or pilules, are made of pure sucrose, lactose, or other polysaccharides. They are formed into small globular masses of various sizes, and are medicated by placing them in a vial and adding the liquid drug attenuation in the proportion not less than one percent (v/w). After shaking, the medicated globules are dried at temperatures not to exceed 40 degrees Centigrade. |
| GRANULE | A small particle or grain. |
| GRANULE, DELAYED RELEASE | A small medicinal particle or grain to which an enteric or other coating has been applied, thus delaying release of the drug until its passage into the intestines. |
| GRANULE, EFFERVESCENT | A small particle or grain containing a medicinal agent in a dry mixture usually composed of sodium bicarbonate, citric acid, and tartaric acid which, when in contact with water, has the capability to release gas, resulting in effervescence. |
| GRANULE, FOR SOLUTION | A small medicinal particle or grain made available in its more stable dry form, to be reconstituted with solvent just before dispensing; the granules are so prepared to contain not only the medicinal agent, but the colorants, flavorants, and any other desired pharmaceutic ingredient. |
| GRANULE, FOR SUSPENSION | A small medicinal particle or grain made available in its more stable dry form, to be reconstituted with solvent just before dispensing to form a suspension; the granules are so prepared to contain not only the medicinal agent, but the colorants, flavorants, and any other desired pharmaceutic ingredient. |
| GRANULE, FOR SUSPENSION, EXTENDED RELEASE | A small medicinal particle or grain made available in its more stable dry form, to be reconstituted with solvent just before dispensing to form a suspension; the extended release system achieves slow release of the drug over an extended period of time and maintains constant drug levels in the blood or target tissue. |

TABLE 12-1-continued

Dosage forms

| NAME | DEFINITION |
|---|---|
| INJECTABLE, LIPOSOMAL | An injection, which either consists of or forms liposomes (a lipid bilayer vesicle usually composed of phospholipids which is used to encapsulate an active drug substance). |
| INJECTION | A sterile preparation intended for parenteral use; five distinct classes of injections exist as defined by the USP. |
| INJECTION, EMULSION | An emulsion consisting of a sterile, pyrogen-free preparation intended to be administered parenterally. |
| INJECTION, LIPID COMPLEX | [definition pending] |
| INJECTION, POWDER, FOR SOLUTION | A sterile preparation intended for reconstitution to form a solution for parenteral use. |
| INJECTION, POWDER, FOR SUSPENSION | A sterile preparation intended for reconstitution to form a suspension for parenteral use. |
| INJECTION, POWDER, FOR SUSPENSION, EXTENDED RELEASE | A dried preparation intended for reconstitution to form a suspension for parenteral use which has been formulated in a manner to allow at least a reduction in dosing frequency as compared to that drug presented as a conventional dosage form (e.g., as a solution). |
| INJECTION, POWDER, LYOPHILIZED, FOR LIPOSOMAL SUSPENSION | A sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution. |
| INJECTION, SUSPENSION, LIPOSOMAL | A liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. |
| INJECTION, SUSPENSION, SONICATED | A liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles. |
| JELLY | A class of gels, which are semisolid systems that consist of suspensions made up of either small inorganic particles or large organic molecules interpenetrated by a liquid-in which the structural coherent matrix contains a high portion of liquid, usually water. |
| KIT | A packaged collection of related material. |
| LINIMENT | A solution or mixture of various substances in oil, alcoholic solutions of soap, or emulsions intended for external application. |
| LIQUID, EXTENDED RELEASE | A liquid that delivers a drug in such a manner to allow a reduction in dosing frequency as compared to that drug (or drugs) presented as a conventional dosage form. |
| LOTION | An emulsion, liquid[1] dosage form. This dosage form is generally for external application to the skin.[2] |
| LOTION, AUGMENTED | A lotion dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| LOZENGE | A solid preparation containing one or more medicaments, usually in a flavored, sweetened base which is intended to dissolve or disintegrate slowly in the mouth. A lollipop is a lozenge on a stick. |
| MOUTHWASH | An aqueous solution which is most often used for its deodorant, refreshing, or antiseptic effect. |
| OIL | An unctuous, combustible substance which is liquid, or easily liquefiable, on warming, and is soluble in ether but insoluble in water. Such substances, depending on their origin, are classified as animal, mineral, or vegetable oils. |
| OINTMENT | A semisolid[3] dosage form, usually containing <20% water and volatiles[5] and >50% hydrocarbons, waxes, or polyols as the vehicle. This dosage form is generally for external application to the skin or mucous membranes. |
| OINTMENT, AUGMENTED | An ointment dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| PASTE | A semisolid[3] dosage form, containing a large proportion (20-50%) of solids finely dispersed in a fatty vehicle. This dosage form is generally for external application to the skin or mucous membranes. |
| PASTILLE | An aromatic preparation, often with a pleasing flavor, usually intended to dissolve in the mouth. |
| PATCH | A drug delivery system that often contains an adhesive backing that is usually applied to an external site on the body. Its ingredients either passively diffuse from, or are actively transported from, some portion of the patch. Depending upon the patch, the ingredients are either delivered to the outer surface of the body or into the body. A patch is sometimes synonymous with the terms 'extended release film' and 'system'. |
| PATCH, EXTENDED RELEASE | A drug delivery system in the form of a patch that releases the drug in such a manner that a reduction in dosing frequency compared to that drug presented as a conventional dosage form (e.g., a solution or a prompt drug-releasing, conventional solid dosage form). |
| PATCH, EXTENDED RELEASE, ELECTRICALLY CONTROLLED | A drug delivery system in the form of a patch which is controlled by an electric current that releases the drug in such a manner that a reduction in dosing frequency compared to that drug presented as a conventional dosage form (e.g., a solution or a prompt drug-releasing, conventional solid dosage form). |
| PELLET | A small sterile solid mass consisting of a highly purified drug (with or without excipients) made by the formation of granules, or by compression and molding. |
| PELLETS, COATED, EXTENDED RELEASE | A solid dosage form in which the drug itself is in the form of granules to which varying amounts of coating have been applied, and which releases a drug (or drugs) in such a manner to allow a reduction in dosing frequency as compared to that drug (or drugs) presented as a conventional dosage form. |
| PILL | A small, round solid dosage form containing a medicinal agent intended for oral administration. |
| PLASTER | Substance intended for external application made of such materials and of such consistency as to adhere to the skin and attach to a dressing; plasters are intended to afford protection and support and/or to furnish an occlusion and macerating action and to bring medication into close contact with the skin. |
| POULTICE | A soft, moist mass of meal, herbs, seed, etc., usually applied hot in cloth that consists of gruel-like consistency. |
| POWDER | An intimate mixture of dry, finely divided drugs and/or chemicals that may be intended for internal or external use. |

TABLE 12-1-continued

Dosage forms

| NAME | DEFINITION |
|---|---|
| POWDER, FOR SOLUTION | An intimate mixture of dry, finely divided drugs and/or chemicals, which, upon the addition of suitable vehicles, yields a solution. |
| POWDER, FOR SUSPENSION | An intimate mixture of dry, finely divided drugs and/or chemicals, which, upon the addition of suitable vehicles, yields a suspension (a liquid preparation containing the solid particles dispersed in the liquid vehicle). |
| SALVE | A thick ointment or cerate (a fat or wax based preparation with a consistency between an ointment and a plaster). |
| SOLUTION | A clear, homogeneous liquid[1] dosage form that contains one or more chemical substances dissolved in a solvent or mixture of mutually miscible solvents. |
| SOLUTION, CONCENTRATE | A liquid preparation (i.e., a substance that flows readily in its natural state) that contains a drug dissolved in a suitable solvent or mixture of mutually miscible solvents; the drug has been strengthened by the evaporation of its nonactive parts. |
| SOLUTION, FOR SLUSH | A solution for the preparation of an iced saline slush, which is administered by irrigation and used to induce regional hypothermia (in conditions such as certain open heart and kidney surgical procedures) by its direct application. |
| SOLUTION, GEL FORMING/ DROPS | A solution, which after usually being administered in a drop-wise fashion, forms a gel. |
| SOLUTION, GEL FORMING, EXTENDED RELEASE | A solution that forms a gel when it comes in contact with ocular fluid, and which allows at least a reduction in dosing frequency. |
| SOLUTION/ DROPS | A solution which is usually administered in a drop-wise fashion. |
| SUPPOSITORY | A solid body of various weights and shapes, adapted for introduction into the rectal orifice of the human body; they usually melt, soften, or dissolve at body temperature. |
| SUPPOSITORY, EXTENDED RELEASE | A drug delivery system in the form of a suppository that allows for a reduction in dosing frequency. |
| SUSPENSION | A liquid[1] dosage form that contains solid particles dispersed in a liquid vehicle. |
| SUSPENSION, EXTENDED RELEASE | A liquid preparation consisting of solid particles dispersed throughout a liquid phase in which the particles are not soluble; the suspension has been formulated in a manner to allow at least a reduction in dosing frequency as compared to that drug presented as a conventional dosage form (e.g., as a solution or a prompt drug-releasing, conventional solid dosage form). |
| SUSPENSION/ DROPS | A suspension which is usually administered in a dropwise fashion. |
| SYRUP | An oral solution containing high concentrations of sucrose or other sugars; the term has also been used to include any other liquid dosage form prepared in a sweet and viscid vehicle, including oral suspensions. |
| TABLET | A solid dosage form containing medicinal substances with or without suitable diluents. |
| TABLET, CHEWABLE | A solid dosage form containing medicinal substances with or without suitable diluents that is intended to be chewed, producing a pleasant tasting residue in the oral cavity that is easily swallowed and does not leave a bitter or unpleasant after-taste. |
| TABLET, COATED | A solid dosage form that contains medicinal substances with or without suitable diluents and is covered with a designated coating. |
| TABLET, COATED PARTICLES | A solid dosage form containing a conglomerate of medicinal particles that have each been covered with a coating. |
| TABLET, DELAYED RELEASE | A solid dosage form which releases a drug (or drugs) at a time other than promptly after administration. Enteric-coated articles are delayed release dosage forms. |
| TABLET, DELAYED RELEASE PARTICLES | A solid dosage form containing a conglomerate of medicinal particles that have been covered with a coating which releases a drug (or drugs) at a time other than promptly after administration. Enteric-coated articles are delayed release dosage forms. |
| TABLET, DISPERSIBLE | A tablet that, prior to administration, is intended to be placed in liquid, where its contents will be distributed evenly throughout that liquid. Note: The term 'tablet, dispersible' is no longer used for approved drug products, and it has been replaced by the term 'tablet, for suspension'. |
| TABLET, EFFERVESCENT | A solid dosage form containing mixtures of acids (e.g., citric acid, tartaric acid) and sodium bicarbonate, which release carbon dioxide when dissolved in water; it is intended to be dissolved or dispersed in water before administration. |
| TABLET, EXTENDED RELEASE | A solid dosage form containing a drug which allows at least a reduction in dosing frequency as compared to that drug presented in conventional dosage form. |
| TABLET, FILM COATED | A solid dosage form that contains medicinal substances with or without suitable diluents and is coated with a thin layer of a water-insoluble or water-soluble polymer. |
| TABLET, FILM COATED, EXTENDED RELEASE | A solid dosage form that contains medicinal substances with or without suitable diluents and is coated with a thin layer of a water-insoluble or water-soluble polymer; the tablet is formulated in such manner as to make the contained medicament available over an extended period of time following ingestion. |
| TABLET, FOR SOLUTION | A tablet that forms a solution when placed in a liquid. |
| TABLET, FOR SUSPENSION | A tablet that forms a suspension when placed in a liquid (formerly referred to as a 'dispersible tablet'). |
| TABLET, MULTILAYER | A solid dosage form containing medicinal substances that have been compressed to form a multiple-layered tablet or a tablet-within-a-tablet, the inner tablet being the core and the outer portion being the shell. |
| TABLET, MULTILAYER, EXTENDED RELEASE | A solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form. |
| TABLET, ORALLY DIS-INTEGRATING | A solid dosage form containing medicinal substances which disintegrates rapidly, usually within a matter of seconds, when placed upon the tongue. |
| TABLET, ORALLY DIS-INTEGRATING, DELAYED RELEASE | A solid dosage form containing medicinal substances which disintegrates rapidly, usually within a matter of seconds, when placed upon the tongue, but which releases a drug (or drugs) at a time other than promptly after administration. |
| TABLET, SOLUBLE | A solid dosage form that contains medicinal substances with or without suitable diluents and possesses the ability to dissolve in fluids. |

TABLE 12-1-continued

Dosage forms

| NAME | DEFINITION |
|---|---|
| TABLET, SUGAR COATED | A solid dosage form that contains medicinal substances with or without suitable diluents and is coated with a colored or an uncolored water-soluble sugar. |

Footnotes:
[1] A liquid s pourable; it flows and conforms to its container at room temperature. It displays Newtonian or pseudoplastic flow behavior.
[2] Previously the definition of a lotion was "The term lotion has been used to categorize many topical suspensions, solutions, and emulsions intended for application to the skin." The current definition of a lotion is restricted to an emulsion.
[3] A semisolid is not pourable; it does not flow or conform to its container at room temperature. It does not flow at low shear stress and generally exhibits plastic flow behavior.
[4] A colloidal dispersion is a system in which particles of colloidal dimension (i.e., typically between 1 nm and 1 μm) are distributed uniformly throughout a liquid.
[5] Percent water and volatiles are measured by a loss on drying test in which the sample is heated at 105° C. until constant weight is achieved.

Example 13

Route of administration. A suitable route of administration for a dosage form containing OSR may be chosen from among those listed in Table 13-1.

TABLE 13-1

Routes of administration

| NAME | DEFINITION |
|---|---|
| BUCCAL | Administration directed toward the cheek, generally from within the mouth. |
| CONJUNCTIVAL | Administration to the conjunctiva, the delicate membrane that lines the eyelids and covers the exposed surface of the eyeball. |
| CUTANEOUS | Administration to the skin. |
| ENDOSINUSIAL | Administration within the nasal sinuses of the head. |
| ENTERAL | Administration directly into the intestines. |
| EPIDURAL | Administration upon or over the dura mater. |
| EXTRACORPOREAL | Administration outside of the body. |
| HEMODIALYSIS | Administration through hemodialysate fluid. |
| INFILTRATION | Administration that results in substances passing into tissue spaces or into cells. |
| INTERSTITIAL | Administration to or in the interstices of a tissue. |
| INTRA-ABDOMINAL | Administration within the abdomen. |
| INTRA-ARTERIAL | Administration within an artery or arteries. |
| INTRA-ARTICULAR | Administration within a joint. |
| INTRACARTILAGINOUS | Administration within a cartilage; endochondral. |
| INTRACAUDAL | Administration within the cauda equina. |
| INTRACORONARY | Administration within the coronary arteries. |
| INTRADERMAL | Administration within the dermis. |
| INTRADUCTAL | Administration within the duct of a gland. |
| INTRADUODENAL | Administration within the duodenum. |
| INTRADURAL | Administration within or beneath the dura. |
| INTRAEPIDERMAL | Administration within the epidermis. |
| INTRAESOPHAGEAL | Administration within the esophagus. |
| INTRAGASTRIC | Administration within the stomach. |
| INTRAGINGIVAL | Administration within the gingivae. |
| INTRALYMPHATIC | Administration within the lymph. |
| INTRAMEDULLARY | Administration within the marrow cavity of a bone. |
| INTRAMENINGEAL | Administration within the meninges (the three membranes that envelope the brain and spinal cord). |
| INTRAMUSCULAR | Administration within a muscle. |
| INTRAOCULAR | Administration within the eye. |
| INTRAOVARIAN | Administration within the ovary. |
| INTRAPERICARDIAL | Administration within the pericardium. |

TABLE 13-1-continued

Routes of administration

| NAME | DEFINITION |
|---|---|
| INTRAPERITONEAL | Administration within the peritoneal cavity. |
| INTRAPLEURAL | Administration within the pleura. |
| INTRAPULMONARY | Administration within the lungs or its bronchi. |
| INTRASINAL | Administration within the nasal or periorbital sinuses. |
| INTRASPINAL | Administration within the vertebral column. |
| INTRASYNOVIAL | Administration within the synovial cavity of a joint. |
| INTRATENDINOUS | Administration within a tendon. |
| INTRATHECAL | Administration within the cerebrospinal fluid at any level of the cerebrospinal axis, including injection into the cerebral ventricles. |
| INTRATHORACIC | Administration within the thorax (internal to the ribs); synonymous with the term endothoracic. |
| INTRATUMOR | Administration within a tumor. |
| INTRAUTERINE | Administration within the uterus. |
| INTRAVASCULAR | Administration within a vessel or vessels. |
| INTRAVENOUS | Administration within or into a vein or veins. |
| INTRAVENOUS BOLUS | Administration within or into a vein or veins all at once. |
| INTRAVENOUS DRIP | Administration within or into a vein or veins over a sustained period of time. |
| INTRAVENTRICULAR | Administration within a ventricle. |
| INTRAVESICAL | Administration within the bladder. |
| INTRAVITREAL | Administration within the vitreous body of the eye. |
| NASAL | Administration to the nose; administered by way of the nose. |
| OPHTHALMIC | Administration to the external eye. |
| ORAL | Administration to or by way of the mouth. |
| OROPHARYNGEAL | Administration directly to the mouth and pharynx. |
| OTHER | Administration is different from others on this list. |
| PARENTERAL | Administration by injection, infusion, or implantation. |
| PERCUTANEOUS | Administration through the skin. |
| PERIARTICULAR | Administration around a joint. |
| PERIDURAL | Administration to the outside of the dura mater of the spinal cord.. |
| PERINEURAL | Administration surrounding a nerve or nerves. |
| PERIODONTAL | Administration around a tooth. |
| RECTAL | Administration to the rectum. |
| RESPIRATORY (INHALATION) | Administration within the respiratory tract by inhaling orally or nasally for local or systemic effect. |
| SOFT TISSUE | Administration into any soft tissue. |
| SUBCONJUNCTIVAL | Administration beneath the conjunctiva. |
| SUBCUTANEOUS | Administration beneath the skin; hypodermic. Synonymous with the term SUBDERMAL. |
| SUBLINGUAL | Administration beneath the tongue. |
| SUBMUCOSAL | Administration beneath the mucous membrane. |
| TOPICAL | Administration to a particular spot on the outer surface of the body. The E2B term TRANSMAMMARY is a subset of the term TOPICAL. |
| TRANSDERMAL | Administration through the dermal layer of the skin to the systemic circulation by diffusion. |
| TRANSMUCOSAL | Administration across the mucosa. |

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A method of supplementing a diet of a mammal, comprising:
    administering to said mammal a pharmaceutically effective amount of a compound having a chemical formula:

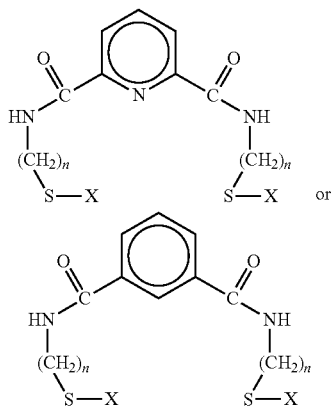

or where n=1-4 and X is selected from the group consisting of hydrogen, lithium sodium, potassium, rubidium, cesium and francium.

2. The method of claim 1, including using oral administration.

3. The method of claim 1, including administering between about 0.5 and about 40 milligrams of said compound per kilogram of said mammal's total body weight per day.

4. The method of claim 1, including using transdermal administration.

5. The method of claim 1, including using nasal administration.

6. The method of claim 1, including using administration by suppository.

7. The method of claim 1, including using intravenous administration.

8. The method of claim 1, including administering said compound with antioxidant.

9. The method of claim 8, including selecting said antioxidant from a list of antioxidants consisting of vitamin-E, vitamin-D, cysteine, glutathione, lipoic acid and combinations thereof.

10. The method of claim 1, wherein said compound has the chemical formula:

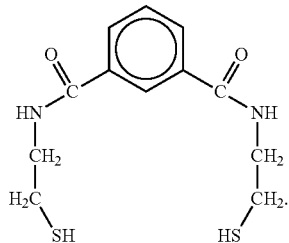

11. The method of claim 10, including using oral administration.

12. The method of claim 10, including administering between about 0.5 and about 40 milligrams of said compound per kilogram of said mammal's total body weight per day.

* * * * *

UNITED STATES PATENT AND TRADEMARK OFFICE
CERTIFICATE OF CORRECTION

PATENT NO. : 9,907,787 B2
APPLICATION NO. : 15/450590
DATED : March 6, 2018
INVENTOR(S) : Boyd E. Haley and Niladri Narayan Gupta Page 1 of 1

It is certified that error appears in the above-identified patent and that said Letters Patent is hereby corrected as shown below:

Claim 1:
Column 29, Line 38, please replace "lithium sodium" with --lithium, sodium--.

Signed and Sealed this
Thirty-first Day of March, 2020

Andrei Iancu
*Director of the United States Patent and Trademark Office*